United States Patent
DeSantis (10) Patent No.: US 12,318,321 B2
(45) Date of Patent: Jun. 3, 2025

(54) SEMI RIGID CERVICAL COLLAR

(71) Applicant: Stephanie DeSantis, Memphis, TN (US)

(72) Inventor: Stephanie DeSantis, Memphis, TN (US)

( * ) Notice: Subject to any disclaimer, the term of this patent is extended or adjusted under 35 U.S.C. 154(b) by 1731 days.

(21) Appl. No.: 15/932,120

(22) Filed: Feb. 6, 2018

(65) Prior Publication Data
US 2018/0243122 A1     Aug. 30, 2018

Related U.S. Application Data (60) Provisional application No. 62/600,743, filed on Feb. 28, 2017.

(51) Int. Cl.
  *A61F 5/00*       (2006.01)
  *A61F 5/055*      (2006.01)

(52) U.S. Cl.
  CPC ..................... *A61F 5/055* (2013.01)

(58) Field of Classification Search
  CPC ............................... A61F 5/055; Y10S 128/23
  USPC ................................... D24/191; 128/DIG. 23
  See application file for complete search history.

(56) References Cited

U.S. PATENT DOCUMENTS

| | | | |
|---|---|---|---|
| 3,374,785 A | 3/1968 | Gaylord, Jr. | |
| 3,507,273 A | 4/1970 | Yellin | |
| 3,696,810 A * | 10/1972 | Gaylord, Jr. | A61F 5/055 |
| | | | 602/18 |
| 4,401,111 A * | 8/1983 | Blackstone | A61F 5/055 |
| | | | 128/DIG. 23 |
| 4,845,810 A | 7/1989 | Brown et al. | |
| 4,872,448 A * | 10/1989 | Johnson, Jr. | A41D 13/0568 |
| | | | 128/DIG. 20 |
| 5,076,264 A * | 12/1991 | Lonardo | A61F 5/3792 |
| | | | 602/17 |
| 5,180,361 A | 1/1993 | Moore et al. | |
| RE34,714 E | 8/1994 | Burns et al. | |
| 5,637,067 A * | 6/1997 | Ausmus | A63B 21/0004 |
| | | | 482/140 |

(Continued)

FOREIGN PATENT DOCUMENTS

| | | | |
|---|---|---|---|
| CN | 20110076777 | 6/2011 | |
| EP | 1488765 A1 * | 12/2004 | ............. A61F 5/055 |

OTHER PUBLICATIONS

Alimed foam cervical collar, admitted prior art https://alimed.com/foan-cervical-collar.html (2 pages).

(Continued)

*Primary Examiner* — Kim M Lewis (57) ABSTRACT

A cervical collar dimensioned to fit a human patient's neck is constructed primarily of foam. It has a foam body with a main top surface and a bifurcated ("M"-shaped) top portion which extends significantly upwardly from the main top surface so as to allow the midline of the occiput to float, thereby minimizing ulceration-causing pressure. The foam body may have a density of at least about 1.4 lbs/ft$^3$, and a mound like bottom projection may extend from a main bottom surface thereof. The foam body may have slits formed in it, and a rigidity-enhancing element is inserted into a slit. By inserting different rigidity-enhancing elements the rigidity of the foam collar may be adjusted. The rigidity-enhancing element may have a C-shape with a hinge spring between two rigid portions.

17 Claims, 8 Drawing Sheets

(56) References Cited

U.S. PATENT DOCUMENTS

| | | | |
|---|---|---|---|
| 6,056,711 A * | 5/2000 | Domanski | A61F 5/055 128/DIG. 23 |
| 7,347,019 B1 | 3/2008 | Shaw | |
| 7,814,579 B2 | 10/2010 | Dion | |
| 7,981,068 B2 | 7/2011 | Thorgilsdottir et al. | |
| 8,679,044 B2 * | 3/2014 | Thorgilsdottir | A61F 5/055 602/19 |
| 2002/0169401 A1 * | 11/2002 | Walpin | A61F 5/055 602/18 |
| 2004/0267178 A1 * | 12/2004 | Benckendorff | A61F 5/055 602/18 |
| 2010/0307512 A1 * | 12/2010 | Krook | A61F 5/56 128/848 |
| 2011/0034844 A1 | 2/2011 | Thorgilsdottir et al. | |
| 2012/0234330 A1 * | 9/2012 | Saiz | A61F 5/56 128/848 |
| 2016/0058600 A1 * | 3/2016 | Basill | A61F 5/055 602/18 |
| 2016/0220410 A1 * | 8/2016 | Hwang | A61F 5/055 |

OTHER PUBLICATIONS

Gold Medical Cervical Collar, Memory Foan, admitted prior art (2 pagtes) https://www.goldmedicalsupplies.com/cervical-collar-comfortable-memory-foam-2-5 width-bc3481/.

DMI Universal Firm Foam Cervical Collars, admitted prior art (3 pages) https://www.walmart.com/ip/DMI-Universal-Firm-Foan-Cervical-Collars-2-1-2-wide/36782315.

* cited by examiner

SEMI RIGID CERVICAL COLLAR

CROSS-REFERENCE TO RELATED APPLICATION

This application is based upon U.S. Provisional Application 62/600,743 filed Feb. 28, 2017, the disclosure of which is hereby incorporated by reference herein.

BACKGROUND AND SUMMARY OF THE INVENTION

Cervical collars are a necessary treatment modality of trauma patients. They are placed to protect a patient's cervical spine until it can be determined that there is no injury, or that there is an injury that requires surgery or further cervical spine bracing.

The most difficult patients to clear are those that are obtunded. There are a few meta-analysis papers in the scientific literature that have been published over the past several years that suggest that it is safe to remove a cervical collar in an obtunded patient if a high quality multi detector CT read by a radiologist is negative. Nevertheless, many physicians are reluctant to adopt this practice for several reasons. Some want additional and stronger evidence before adopting this practice, while others do not trust the quality of the imaging and interpretation available to them, or may have personal experience of seeing an "exception" that makes them want to be more cautious. In today's volatile medical legal environment in the United States, many physicians feel especially at risk in making this determination based on CT alone, and want to wait until either an MRI can be performed or the patient is alert enough to rely on a physical exam. An MRI shows the soft tissues better, and can show problems such as ruptured discs, ligament or disc tears, or intra-spinal hemorrhages that cannot be readily seen on CT scans.

There are multiple reasons why there can be a significant delay in obtaining an MRI, such as the presence of orthopedic traction, an intracranial pressure monitor, a pacemaker, or simply the patient is just too unstable. Thus, patients can sometimes lie around in a rigid cervical collar for several days or weeks until the status of their cervical spine can be determined with reasonable medical certainty, enhancing the probability of the formation of pressure ulcers in the patient's skin.

The incidence of pressure ulcers associated with the use of cervical collars in hospitalized patients varies from 1% to 38% in the literature. At Region One Health Hospital in Memphis, Tennessee, the $4^{th}$ busiest Level One trauma center in the US, 20-30% of all pressure ulcers occurring in the hospital for the years 2012-2016 have been occipital in location, and most were associated with the use of a rigid cervical collar.

The occurrence of pressure ulcers has all too often been considered an undesirable but somewhat unavoidable complication of the use of cervical collars, as the neurologic consequences of missing an unstable cervical spine injury can be devastating. However, new performance requirements applied to hospitals that are tied to reimbursement have caused hospitals to refocus on measures to reduce the incidence of all pressure ulcers. Thus, hospital administrators are putting more pressure on physicians and nurses to do whatever they can to reduce the number of pressure ulcers occurring. Nursing measures are very important in prevention, but sometimes that is difficult to accomplish or is just not enough in a high risk population.

Many of the obtunded patients who are left in cervical collars awaiting spine clearance are patients who have a negative cervical CT or have a minor cervical fracture that is usually not unstable. This subset of patients is potentially unnecessarily incurring occipital pressure ulcers. The patients with negative cervical CT's are especially at low risk for incurring a new neurologic deficit from an unstable ligamentous injury while lying in bed unconscious on a ventilator. If the physician responsible for clearing that patient's cervical spine is uncomfortable doing so until an MRI or physical exam can be accomplished, then that patient could be reasonably immobilized while in bed in a less rigid orthotic for protection. A "semi rigid" cervical stabilization orthotic could be restricted to use while the patient was in bed, and a more rigid collar could be replaced when the patient is mobilized upright out of bed.

There are other patients in a hospital, rehabilitation, or nursing home situation who might benefit from the use of a semi rigid cervical collar with good occipital and chin padding as well. These patients may not have a cervical spine injury, but their cervical musculature may be so weakened by a significant illness or stroke that they need help keeping their head in alignment when mobilized out of bed to a chair. Often these patients recovering from a serious and sometimes prolonged illness have poor skin quality from inadequate nutrition, and are more vulnerable to pressure ulceration as well.

There are other potential uses for a semi rigid, more comfortable, but economical cervical system outside of the hospital setting as well. Many patients who are prescribed treatment in a rigid cervical collar often complain of more discomfort wearing the rigid collars than without and so often do not comply, but still remain in pain. There are definitely subsets of patients with injuries who would be safe to treat in a semi rigid, more comfortable cervical collar system. Patients with cervical strain injuries, or certain minor cervical spine fractures such as spinous process fractures or transverse process fractures, are often placed in a rigid cervical brace for pain control, but are generally not considered to really need rigid immobilization. Those types of patients would be appropriately managed in a semi rigid cervical collar, at the discretion of their neurosurgeon or orthopedic surgeon.

While the need to minimize the incidence of ulcers in individuals requiring a cervical collar, for whatever reason, has long been recognized in the art (e. g. see U.S. Pat. Nos. 5,180,361 and 7,981,068) the incidence of ulcerations is still unacceptably high and devices which seek to address it are often very complicated and expensive. According to the present invention, a semi-rigid cervical collar is provided that is simple in design and materials so that it is cost-effective yet performs well as a cervical collar (especially for "bed only" patients) while simultaneously minimizing the probability that the patient will develop skin ulcerations as a result of the pressure applied to the patient's body, especially her or his occiput and chin.

The desirable results according to the invention are accomplished by providing significantly more foam in contact with the patient's body than in conventional "hard" cervical collars, and by configuring the rear of the collar to allow the midline of the occiput to "float," thereby minimizing direct pressure to an area that is a common site of pressure ulceration. The materials utilized also minimize moisture trapping that encourages the formation of pressure sores, and the semi-rigid nature of the collar of the invention helps to minimize pressure ulcer-development caused by swelling of tissues of the scalp and neck, which are often associated with fresh injuries. The collar of the invention is expected to allow more small movements of the head and cervical spine compared to properly fitted and tightened conventional hard cervical collars, and is particularly desirable for use with patients who are strongly not suspected of having highly unstable cervical spine injuries. However, other—somewhat more rigid—versions of the invention can also be provided, and in fact one basic structure can be easily modified to provide varying degrees of support.

While there have been many uses of foam per se in proposed prior art collars, such as shown in U.S. Pat. Nos. 3,374,785 and 3,507,273, and U.S. Patent Publication 2011/0034844, including some with semi-rigid or rigid interior sheets (e. g. Re. 34,714), none of the prior art devices have had the combination of simplicity, effectiveness, ulcer-minimization, and flexibility (including rigidity adjustability), of cervical collars according to the invention. Also, the invention has the advantage that it is similar enough to foam cervical collars on the market (such as those of DMI, Gold Medical, and Ahmed) that FDA approval should be relatively simple, while at the same time having significant advantages over presently marketed foam collars. Among the significant differences are that the "M" shape is in the back and is tall enough so as to support the occiput. In the foam collars on the market, on the other hand, any "M" shape is where the chin rests, so the hook and loop (e. g. Velcro®) closure is usually in the back.

According to one aspect of the invention a cervical collar is provided that is constructed primarily of semi-rigid foam. The foam should have at least enough stability for in bed patients (e. g. EVA foam with a density of at least about 1.4 lbs/ft$^3$) while at the same time minimizing the probability that ulceration will occur as a result of collar pressure on an area that is a common site of pressure ulceration. The collar preferably attaches at the front with conventional hook and loop (e. g. Velcro®) fasteners (or other types of conventional strap fasteners) and at the rear has a bifurcated (generally "M" shaped) top portion that extends significantly upwardly from the main foam body of the collar so as to allow the midline of the occiput to float, thereby minimizing ulceration-causing pressure.

Various degrees of rigidity can be provided for the collar of the invention by providing an insert in the foam body, which foam body has both longitudinal and vertical slits. The insert preferably is of a hard plastic that may have a C-shape which is either substantially in strip form, or is contoured to have a shape similar to the foam body minus the rear bifurcated top portion. A hinge spring may optionally be provided for two halves of the insert to bias the collar toward a "closed" position. The insert is preferably inserted into the foam body through a slit in the rear of the main body which intersects with a longitudinal slit, typically below the bifurcated top portion, and is removable. By providing inserts of varying thickness and/or materials the rigidity and like properties of the cervical collar of the invention may be readily changed. The inserts may have openings therein to improve breathability, as may the foam body. Alternatively, the foam body may be molded around an insert, in which case it is not removable.

It is the primary object of the present invention to provide semi-rigid immobilization and support of the neck of a patient while minimizing the formation of pressure ulcers on the head of the patient. This and other objects of the invention will become clear from the detailed description of the drawings, and the appended claims.

BRIEF DESCRIPTION OF THE DRAWINGS

FIG. 2 is a side view of the laid out collar of FIG. 1 (without the hook and loop fastener strips);

FIG. 3A is a top schematic perspective view of the collar of FIG. 1 when in an operative, closed, position around a patient's neck (not shown), while

DETAILED DESCRIPTION OF THE DRAWINGS

The foam-only embodiment of the semi-rigid cervical collar 10 of FIGS. 1-4 is dimensioned to fit on a human patient's neck and has a main primarily or substantially exclusively foam body 12 with a back 14 (FIGS. 1-4), front 15 (FIGS. 2-4), main top surface 16, and main bottom surface 17. Hook and loop (e. g. Velcro®) fasteners (or other conventional fasteners) in the form of a first strip 19 and a second strip 20 are affixed by any conventional mechanism (e. g. stitching or adhesive) to the back surface 14 of the foam body 12 of the collar 10 (adjacent the ends 24, 25 thereof), one of the strips 19, 20 having hook fasteners, the other loop. A piece of foam 22 can be provided over the hooks/loops of the interior of the strip 19 so that hooks or loops cannot come into contact with the patient's body. When the collar 10 is in the closed position around a patient's neck (see FIG. 3A) an opening 26 is provided between the ends 24, 25 thereof to allow easy access for a possible tracheostomy.

Figures 2, 3A:
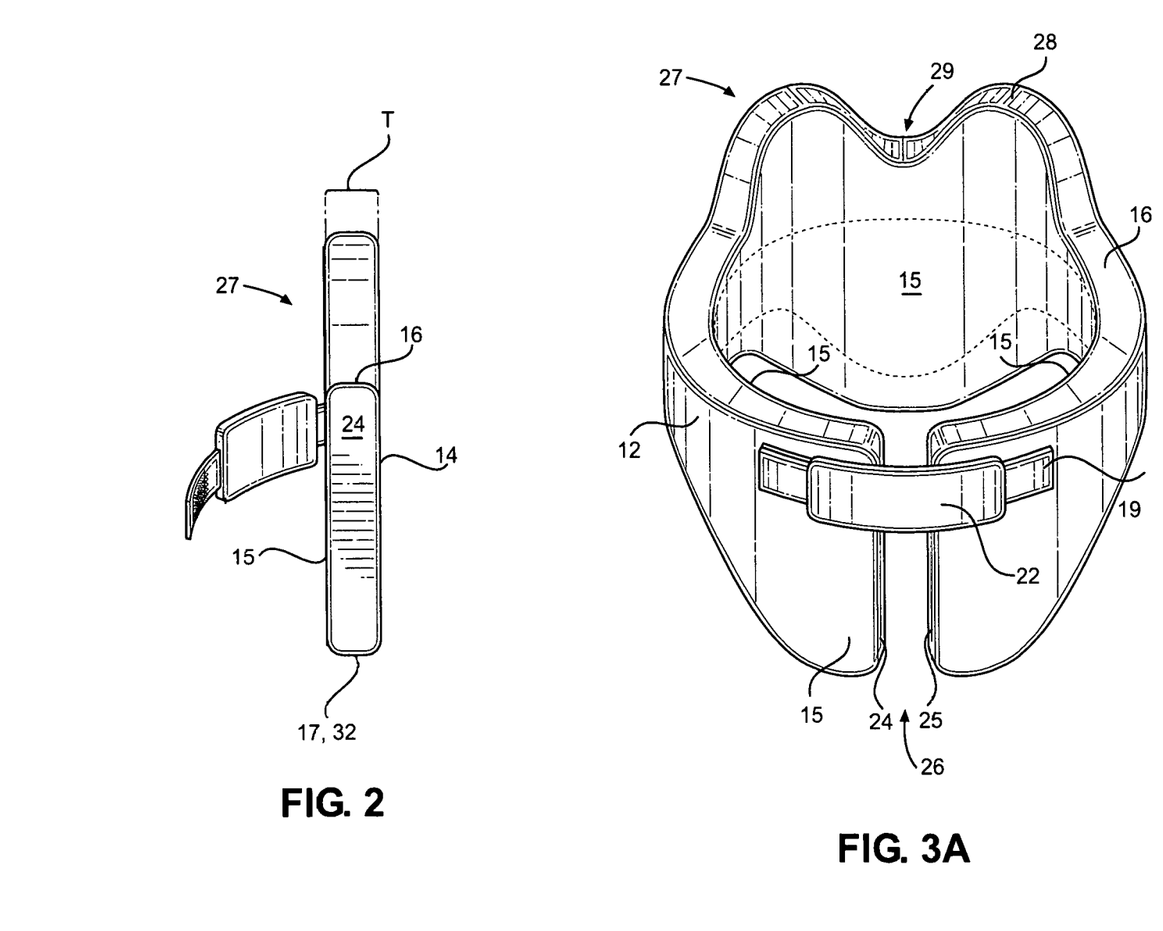
Figure 3B:
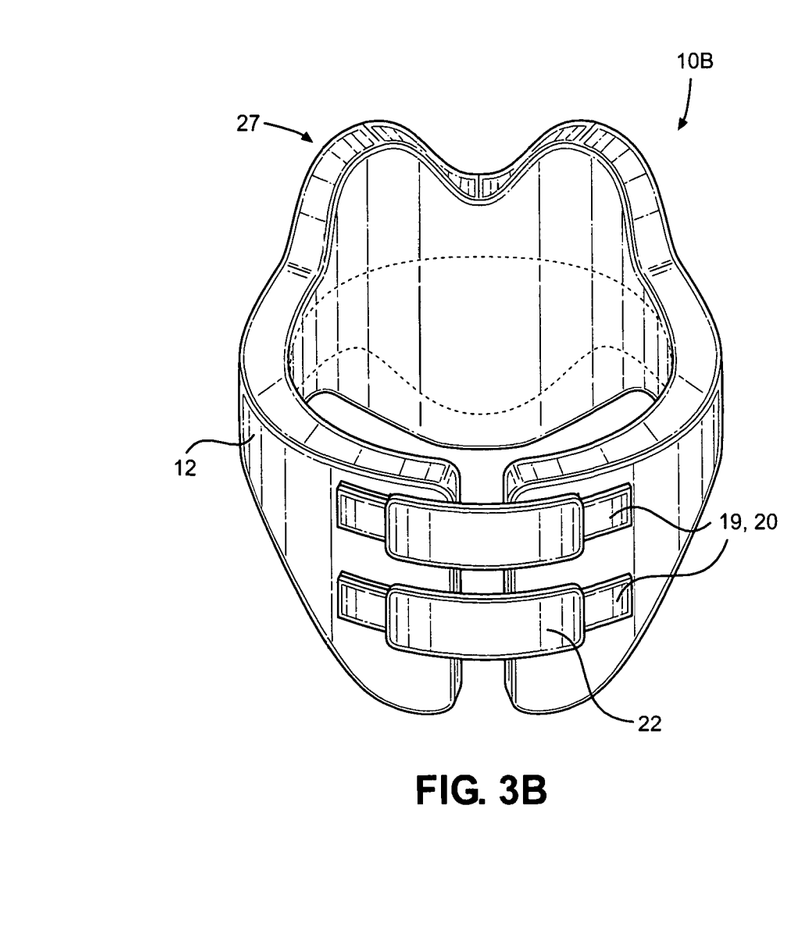
FIGS. 3B-3D are views like FIG. 3A of slightly modified forms of an exemplary cervical collar according to the invention.
Figure 3C:
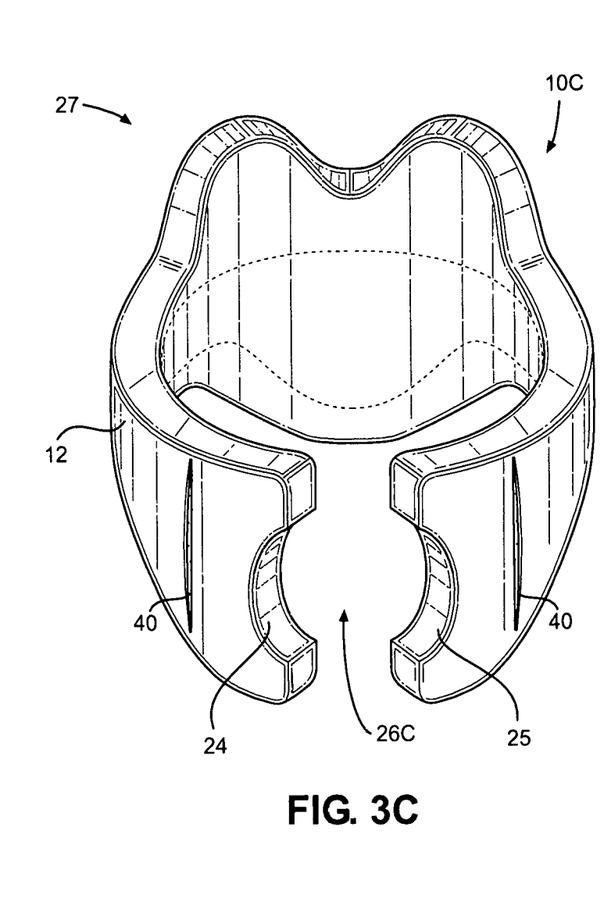
Figure 3D:
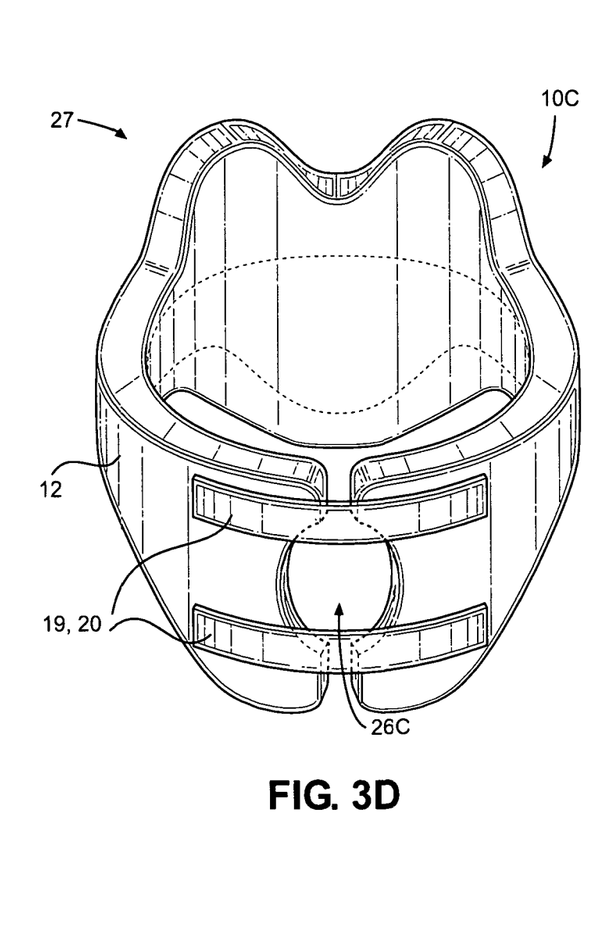
Figure 4:
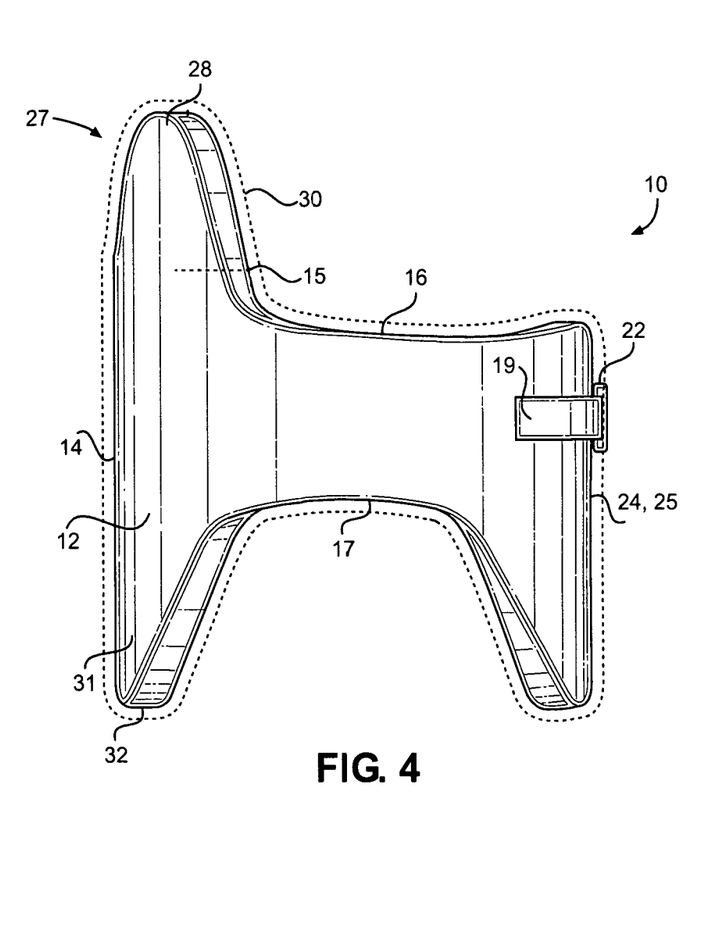
FIG. 4 is a right side view (as viewed in FIG. 3A) of the collar of FIG. 3A in operative, closed, position.

The collar 10b of FIG. 3B is the same as the collar 10 of FIG. 3A except that two sets of hook and loop fasteners 19, 20 (or other suitable fastening strips) are provided. When two sets of fasteners 19, 20 are provided, to allow easy access for a possible tracheostomy a central opening 26c may be provided in the ends 24, 25 of the foam body 12 of the modified form of collar, 10c. FIG. 3C shows the opening 26c clearly, while FIG. 3D shows it with fastening strips 19, 20 above and below it.

The foam forming the body 12 may be of a number of different types, however the preferred type is an open cell foam, such as high density polyurethane or polyethylene (EPE) foam. Closed cell foams, such as ethylene-vinyl acetate (EVA) foam, also may be suitable. Regardless of foam type, the foam forming the body 12 should have a density of at least about 1.4 lbs/ft$^3$ (e. g. about 2.8). The density of the body 12 will be chosen so that, for the dimensions utilized, it has sufficient support properties for the patient's size and condition yet is appropriately deformable so as to minimize the pressure on the patient's skin.

The density of the foam strip 22 can be of a significantly lower density, however, since it doesn't provide any structural support but is just for protection of the patient's skin. In fact another material, such as soft cloth, may be utilized in place of foam for the strip 22. Also the front 15 of the collar 10 may be covered with a soft cloth sleeve (as in U.S. Pat. No. 3,374,785) so as to wick away moisture, or it may be covered with a plastic coating to prevent moisture from penetrating the foam body 12, if desired. Alternatively, the entire collar may be covered with a soft cloth sleeve, as shown schematically in dotted line at 30 in FIG. 4.

The dimensions of the collar 10 must be such so that the foam body 12 has sufficient structural integrity to function as a cervical collar. Typical dimensions include a thickness T (FIG. 2) of about ½-3 inches (1.25-7.6 cm) depending on the size of the patient, type and density of foam, and other parameters; a length of each of the faces 24, 25 of about 1½-10 inches (4-25 cm); and a length of each half of the main top surface 16 of about 1½-15 inches (4-38 cm). The height H (FIG. 1) of the main portion of the body 12, between the ends 24, 25 and the top and bottom surfaces 16, 17, is preferably about 1-7 inches (2.5-17.5 cm).

A highly desirable feature of the collar 10 of the invention is the provision of the bifurcated top portion 27, between the halves of the main top surface 16. The bifurcated (essentially "M"-shaped) top portion 27 extends significantly (e. g. about 1-4 inches, or 2.5-10 cm) upwardly from the main top surface 16 of the foam body 12 so as to allow the midline of the occiput to float, thereby minimizing ulceration-causing pressure. Each projection 28 of the bifurcated top portion 27 may have a width of about 1-5 inches (2.5-12.5 cm), and the valley 29 between the projections 28 may have a width of about ¾-3 inches (2-7.6 cm).

Figure 1:
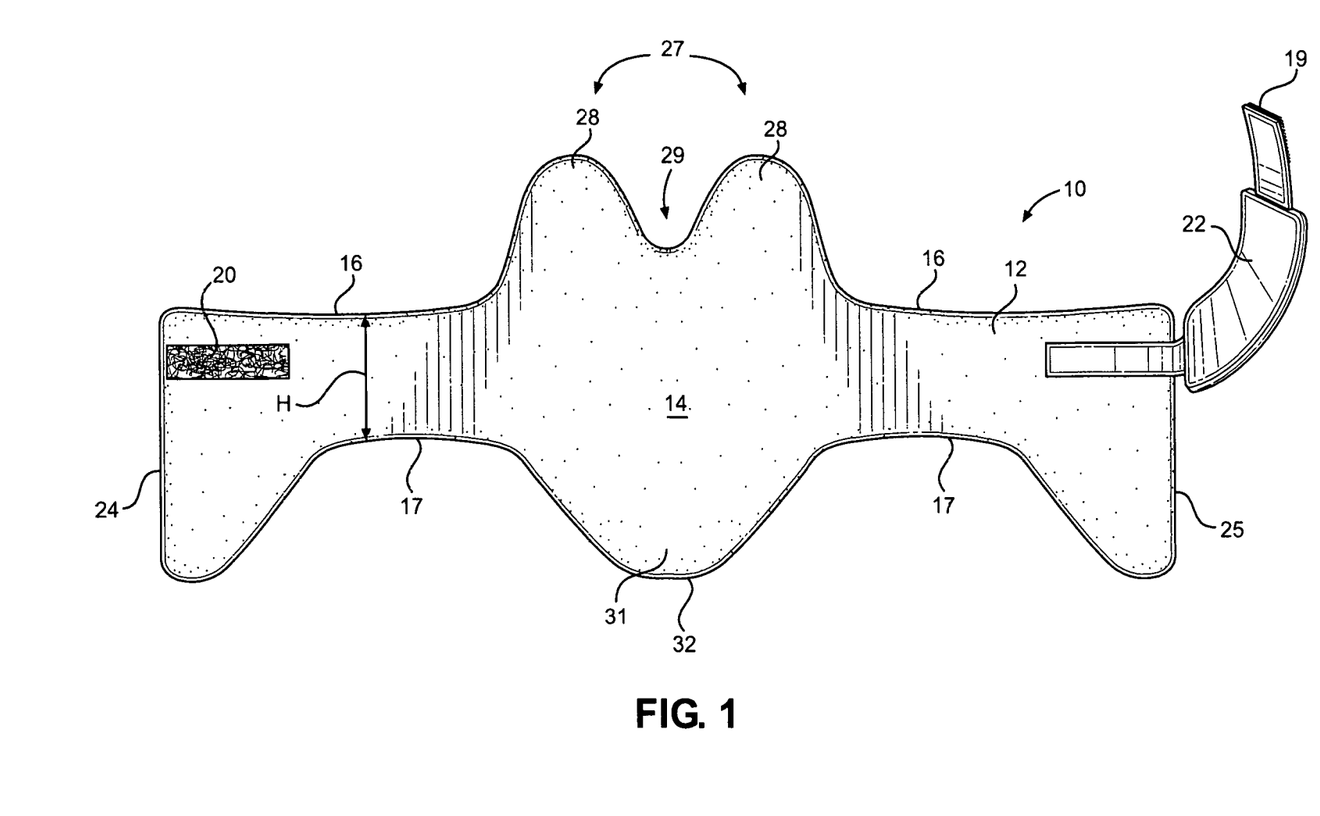
FIG. 1 is a plan view of the back of a foam-only embodiment of a semi-rigid cervical collar according to the invention when laid out ("open")

The collar 10 also may be contoured, as best seen in FIG. 1, so that at the center of the bottom surface 17 there is a projection 31 having a maximum height/tip 32 vertically aligned with the valley 29 of the bifurcated top portion 27. The tip 32 is preferably about 1½-8 inches (3.8-20 cm) from the main bottom surface 17. The projection 31 preferably has the rounded, "mound," type shape illustrated in FIG. 1.

Figure 5:
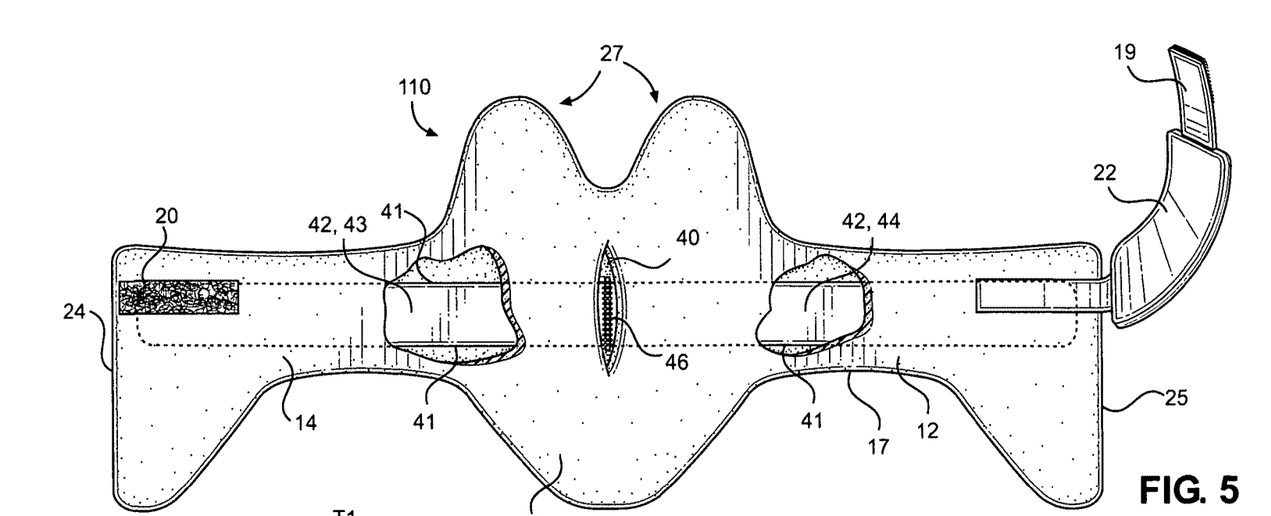
FIG. 5 is an open back view, like that of FIG. 1, of another embodiment of a cervical collar according to the invention in which a removable rigidity-enhancing strip (shown primarily in dotted line in FIG. 5), with a hinge spring, is provided within the hollow interior of the foam collar.

While the collar 10 of FIGS. 1-4 is highly suited for obtunded patients, or those known to have minor cervical issues, in some circumstances it will be desirable to have a similar cervical collar for patients needing more support. The collar 110 of FIGS. 5 & 6 is suitable for such purposes. [In FIGS. 5 & 6 components comparable to those of the FIGS. 1-4 embodiment are shown by the same reference numeral.]

The foam body 12 of the collar 110 has an external vertical slit 40 provided in the center of the back surface 14 thereof of sufficient dimension and extent (e. g. about ½ depth of the foam body 12 thickness) to allow the insertion of a rigidity-enhancing plastic or metal strip 42 (FIGS. 5 & 6) therein. A cutting tool is provided that enters the body 12 through the slit 40 to provide interior longitudinal slits 41 (see cut-out areas in FIG. 5) within the body 12 substantially parallel to the main top surface 16. The interior slits 41 are just large enough to accommodate the strip 42. The strip 42 is shown primarily in dotted line in FIG. 5 except where the foam body 12 is cut away to reveal the strip 42 in the interior slits 41. The strip 42 is preferably made of a conventional plastic with structural integrity (such as polyethylene [high, low, or medium density], polypropylene, or pvc) that is capable of being molded into the curved shape illustrated in FIG. 6, and it may be solid or apertured. While the strip 42 may be one piece and substantially C-shaped (as illustrated in FIG. 6) the strip 42 may comprise two curved halves, 43, 44, each roughly half of a C-shape, and connected together by a conventional hinge spring, shown schematically at 46 in FIGS. 5 & 6.

Figure 6:
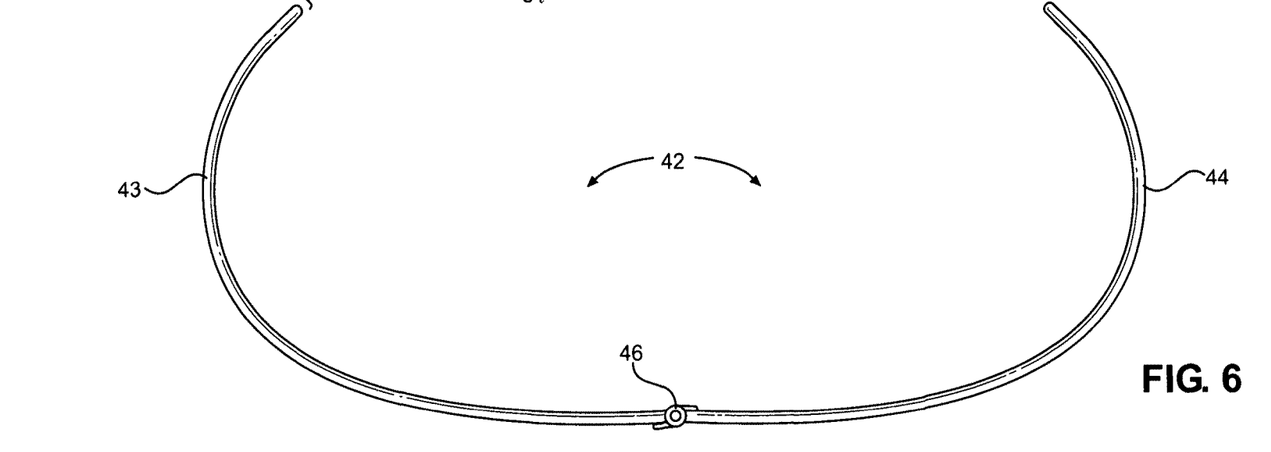
FIG. 6 is a top plan view of the strip, with hinge spring, per se, of FIG. 5.

The hinge spring 46 biases the curved portions 43, 44 of the strip 42 toward the "closed" position (that is wrapping around the patient's neck), as illustrated in FIG. 6. The hinge spring 46 may be of any conventional type such as (without limitation) shown per se in U.S. Pat. Nos. 4,845,810, 7,347,019, or 7,814,579 (element 90), or U.S. Patent Publication 2012/0168047 (element 322).

Typical desirable dimensions of the substantially rectangular strip 42, depending upon the exact material of which it is made and how rigid it is desired to be, include a thickness T1 (FIG. 6) of about 2-4 mm, and a height (the dimension parallel to slit 41 in FIG. 5) of about ½-2 inches (1.25-5 cm). By changing the material and dimensions of the strip 42 one can adjust the rigidity of the collar 110 while still providing the advantages of its basic foam construction which minimizes pressure ulceration of the patient's skin. The strip 42 may be removed through the slit 40 and replaced with another strip 42 having different rigidity.

FIG. 3C shows another possible location for a slit 40 into which a suitable plastic insert may be inserted.

Figure 7:
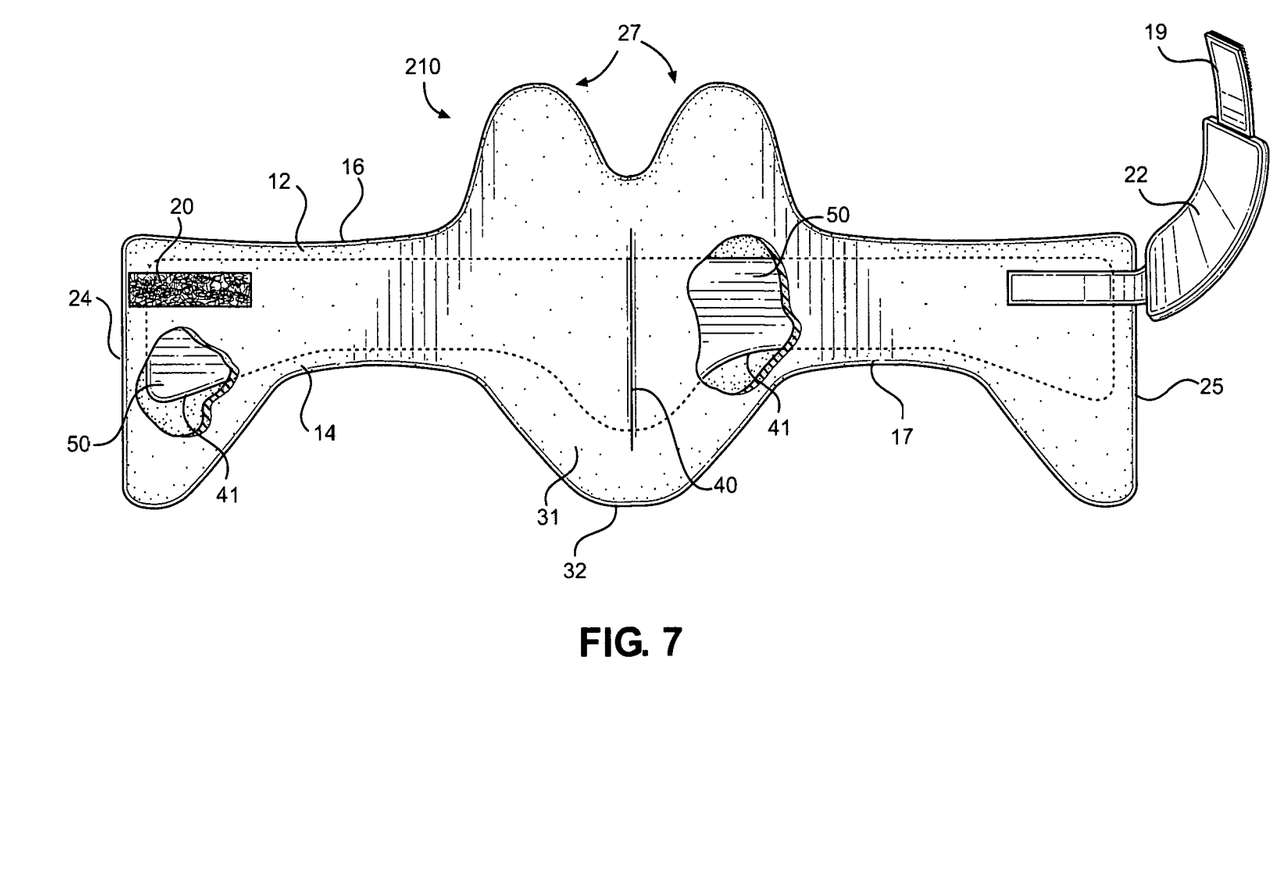
FIG. 7 is a view like that of FIG. 5 of a cervical collar of another embodiment of the invention in which the insert has a different foam body-simulating configuration and no hinge spring.

FIG. 7 shows another embodiment of cervical collar 210 according to the invention which has a different configuration of the rigidity-enhancing member than that of the strip 42. [In FIG. 7 components comparable to those of the FIGS. 1-6 embodiments are shown by the same reference numeral.] In the FIG. 7 embodiment the rigidity-enhancing element comprises the contoured plastic or metal body 50, shown primarily in dotted line in FIG. 7 except where the foam body 12 is cut away. Like the strip 42 the body 50 preferably has a generally C-shape when viewed in plan, but is distinct from the strip 42 because it has a configuration that simulates that of the body 12 (minus the top portion 27), as clearly seen in FIG. 7.

The slits 40, 41 in the FIG. 7 embodiment must be significantly longer than in the FIG. 5 embodiment to accommodate the larger height of portions of the contoured body 50. The body 50, like the strip 42, has a thickness of about 2-4 mm, and the material and thickness thereof may be modified to provide the desired rigidity. In view of the more extensive nature of the body 50 it preferably is in one integral piece, and thus there is no need for a hinge spring, although it can be formed in two pieces with a hinge spring.

In some circumstances, where adjustability is not important, the body 50 or strip 42 may be integrally molded with the foam body 12.

Figure 8:
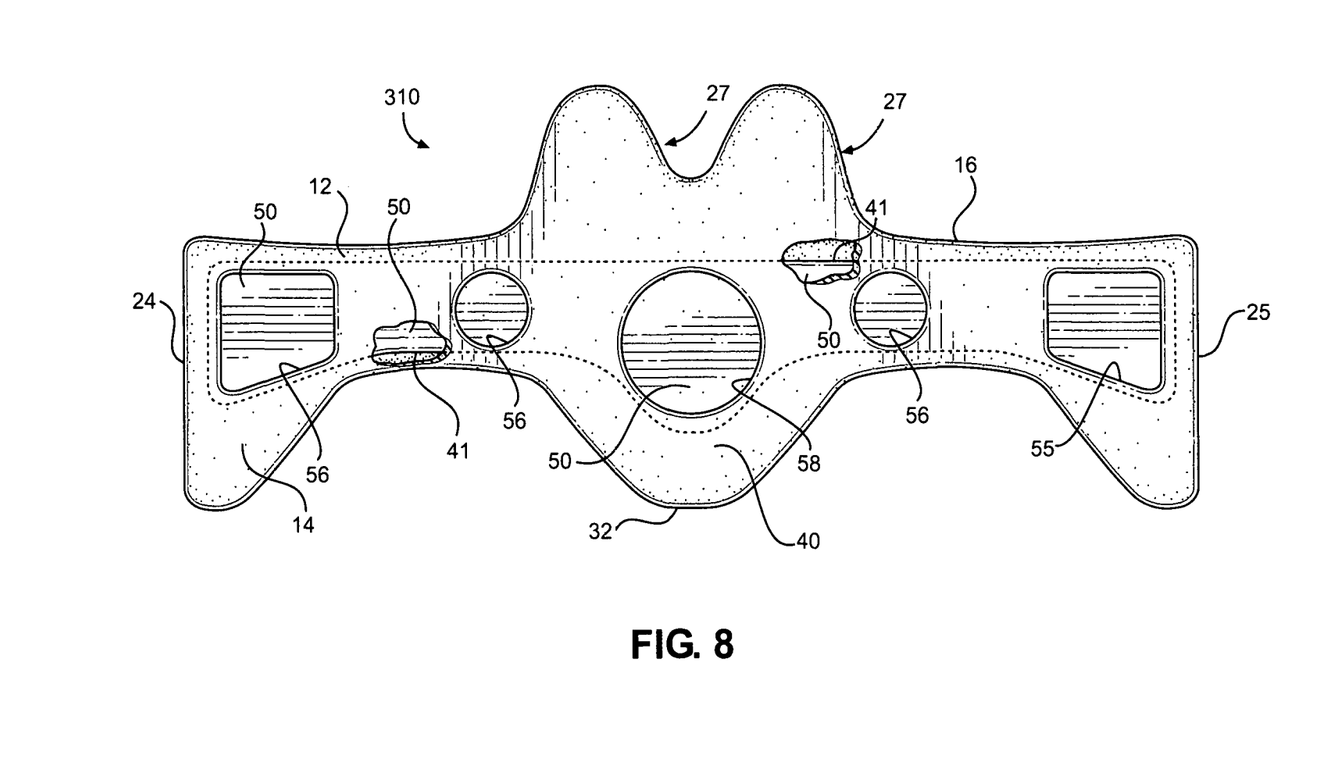
FIG. 8 is a view like that of FIG. 7 of another embodiment of cervical collar according to the invention.

The collar 310 of FIG. 8 is substantially identical to the collar 210 except that, in order to provide better "breathability" of the collar (including so that it is not as hot for the patient) various openings or perforations 56 are provided at various points. [In FIG. 8 components comparable to those of the FIGS. 1-7 embodiments are shown by the same reference numeral.] For ease of illustration the one set or a plurality of sets of fastening straps (19, 20 in the other drawings) are not shown. While the straps may be flat, as is conventional, they alternatively could be contoured.

An enlarged central opening 58 takes the place of the slit 40, and allows insertion of the rigidity-enhancing body 50 into the foam body 12.

Figure 9:
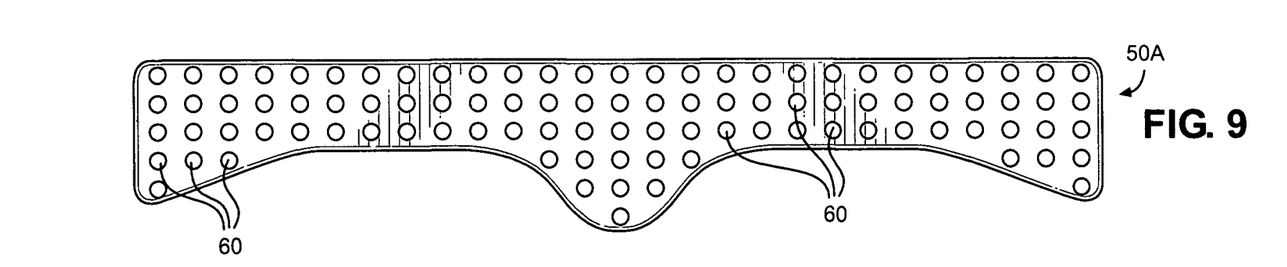
FIGS. 9 & 10 are plan views of different types of rigidity-enhancing structures that may be utilized with the collars of FIG. 5, 7, or 8.
Figures 10, 11:
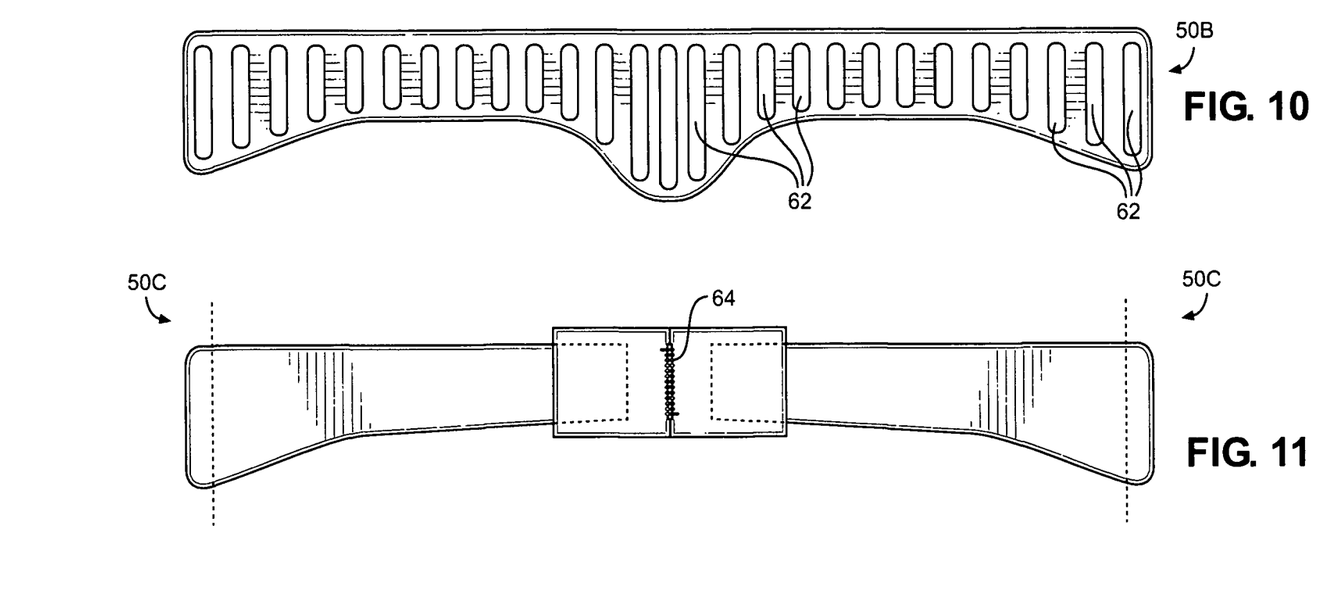
FIG. 11 is a plan view of another multi-piece form of rigidity-enhancing insert that may be utilized with any of the collars shown.

FIGS. 9 and 10 show two different embodiments of rigidity-enhancing bodies 50A, 50B, that are similar to the body 50 except that they include perforations 60 (in the case of body 50A of FIG. 9), slots 62 (in the case of body 50B of FIG. 10), or like openings that enhance "breathability" of the cervical collar 310. The rigidity-enhancing bodies 50A, 50B may be inserted into the foam body 12 (as for the body 50 of FIGS. 7 & 8) or they may be attached to the outside of the back 14 of the foam body 12, as by adhesive, stitching, ultrasonic welding, or another conventional technique.

FIG. 11 shows another embodiment in which the rigidity-enhancing insert 50C is in two parts, with a separate piece 64 between the two parts 50C. The piece 64 could be hinged to the insert parts 50C. The separate piece 64 would join the other two parts 50C at the back of the collar, perhaps through another slit (not shown).

The ranges given above are to be interpreted to encompass all included ranges within a broader value. For example a dimension of about 1-4 inches includes (in inches) 0.95-3, 2.1-4.05, 2.6-3.6, and all other narrower ranges within the broad range.

The invention is to be accorded the broadest interpretation of the appended claims consistent with the prior art to encompass all equivalent structures and methods.

What is claimed is:

1. A cervical collar dimensioned to fit a human patient's neck and occiput, which occiput has a midline: said cervical collar being primarily of foam, having a foam body with a main top surface and comprising a bifurcated top back portion which extends significantly upwardly from the main top surface so as to allow the midline of the occiput to float, thereby minimizing ulceration-causing pressure; and fasteners at a portion remote from said bifurcated top back portion to hold said cervical collar in place surrounding and supporting a patient's neck and wherein the foam body has slits formed therein, and a rigidity-enhancing entirely within said foam body inserted in one of the slits.

2. A cervical collar as recited in claim 1 wherein the foam body has a mound like bottom projection from a main rear bottom surface thereof.

3. A cervical collar as recited in claim 1 wherein the rigidity-enhancing element is selected from the group consisting essentially of a generally C-shaped element comprising a rigid strip with a hinge spring, and a rigid body contoured to simulate the approximate shape of the foam body.

4. A cervical collar as recited in claim 1 wherein the rigidity-enhancing element is a generally C-shaped element comprising a rigid strip with a hinge spring.

5. A cervical collar as recited in claim 1 wherein the rigidity-enhancing element comprises a rigid body contoured to simulate the approximate shape of the foam body.

6. A cervical collar as recited in claim 1 wherein the bifurcated portion extends about 1-4 inches upwardly from the main top surface of the foam body so as to allow the midline of the occiput to float, thereby minimizing ulceration-causing pressure.

7. A cervical collar as recited in claim 6 wherein the bifurcated top back portion has two projections; and wherein each projection of the bifurcated top back portion has a width of about 1-4 inches, and the valley between the projections has a width of about ¾-3 inches.

8. A cervical collar as recited in claim 7 wherein the rigidity-enhancing element is selected from the group consisting essentially of a generally C-shaped element comprising a rigid strip with a hinge spring, and a rigid body contoured to simulate the approximate shape of the foam body.

9. A cervical collar as recited in claim 1 wherein said foam body is substantially completely made of foam.

10. A cervical collar as recited in claim 1 wherein the rigidity-enhancing element is of metal or hard plastic with a thickness of about 2-4 mm.

11. A cervical collar dimensioned to fit on, surround, support, and stabilize a human patient's neck comprising a foam body with slits formed therein, and a surrounding and supporting rigidity-enhancing element entirely within said foam body inserted into one or more slits.

12. A cervical collar as recited in claim 11 wherein the rigidity-enhancing element is a generally C-shaped element comprising a rigid strip with a hinge spring.

13. A cervical collar as recited in claim 11 wherein the rigidity-enhancing element comprises a rigid body contoured to simulate the approximate shape of the foam body.

14. A cervical collar as recited in claim 11 wherein the rigidity-enhancing element is of metal or hard plastic with a thickness of about 2-4 mm.

15. A method of utilizing a primarily foam body cervical collar for fitting on, surrounding, supporting, and stabilizing a patient's neck by changing the rigidity thereof by inserting different rigidity-enhancing elements of different rigidity through a slit in the foam body so as to be entirely within the foam body.

16. A method as recited in claim 15 wherein the rigidity-enhancing elements comprise generally C-shaped elements comprising a rigid strip with a hinge spring.

17. A method as recited in claim 15 wherein the rigidity enhancing elements comprise rigid bodies contoured to simulate the approximate shape of the foam body.

* * * * *